United States Patent [19]

Heitmann et al.

[11] Patent Number: 5,175,347
[45] Date of Patent: Dec. 29, 1992

[54] PROCESS FOR PREPARING CIS-DIHYDRONOPOL

[75] Inventors: Walter Heitmann, Marietta, Ga.; Uwe Maetzel, Burgdorf, Fed. Rep. of Germany

[73] Assignee: Kali-Chemie Pharma GmbH, Hanover, Fed. Rep. of Germany

[21] Appl. No.: 801,658

[22] Filed: Dec. 2, 1991

Related U.S. Application Data

[63] Continuation of Ser. No. 548,829, Jul. 6, 1990, abandoned.

[30] Foreign Application Priority Data

Jul. 7, 1989 [DE] Fed. Rep. of Germany ....... 3922386

[51] Int. Cl.⁵ .................. C07C 17/02; C07C 35/22; C07C 35/24; C07C 35/26
[52] U.S. Cl. ................................ 560/256; 568/820
[58] Field of Search .................. 560/256; 568/820

[56] References Cited

U.S. PATENT DOCUMENTS 3,845,048  10/1974  Baronnet .......................... 544/174

FOREIGN PATENT DOCUMENTS 2097031  8/1973  France .
1351505  5/1974  United Kingdom .
2019841  7/1979  United Kingdom .
2424244  11/1979  United Kingdom .

*Primary Examiner*—Jose G. Dees
*Assistant Examiner*—Joseph M. Conrad, III
*Attorney, Agent, or Firm*—Foley & Lardner

[57] ABSTRACT

A process for preparing cis-dihydronopol and esters thereof in which corresponding esters of (-)nopol are stereoselectively hydrogenated by heterogeneous hydrogenation in the presence of a platinum, platinum oxide or ruthenium/carbon catalyst, and the resulting cis-dihydronopyl esters optionally may be converted into corresponding alcohols by hydrolysis.

4 Claims, No Drawings

PROCESS FOR PREPARING CIS-DIHYDRONOPOL

This application is a continuation of application Ser. No. 07/548,829, filed Jul. 6, 1990 now abandoned.

BACKGROUND OF THE INVENTION

The present invention relates to a process for preparing cis-dihydronopol (=2-((1S,2S,5S)-6,6-dimethylbicyclo[3.1.1]hept-2-yl)-ethanol) and its lower carboxylic or benzoic esters. Dihydronopol is a 2-(6,6-dimethylbicyclo[3.1.1]hept-2-yl)-ethanol of formula A

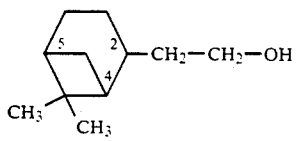
(A)

Formula A contains, in positions 1, 2 and 5 of the ring structure, asymmetric centers which can each be in the R or S configuration, so that the substances can occur in several stereoisomeric forms.

Dihydronopol is derived from the natural terpene (−)-β-pinene (=(1S,5S)-6,6-dimethyl-2-methylenebicyclo[3.1.1]heptane) of formula B

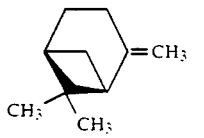
(B)

in which the asymmetric centers in the 1 and 5 positions have the S configuration. Accordingly, the asymmetric centers in the 1 and 5 positions in dihydronopol also have the S configuration, while the center in the 2 position can have the S or R configuration. Thus, the substituent in the 2 position in cis-dihydronopol is cis with respect to the dimethylmethylene bridge and in trans-dihydronopol is trans with respect thereto.

Dihydronopol is disclosed in French Patent No. 2,097,031 as an intermediate for preparing pharmacologically active substances. For example, dihydronopol is an intermediate for preparing pinaverium bromide which is commercially available as a spasmolytic (N-(2-bromo-4,5-dimethoxybenzyl)-N-{2-[2-((1S,5S)-6,6-dimethylbicyclo[3.1.1]hept-2-yl)-ethoxy]-ethyl}-morpholinium bromide="Dicetel ™"). To prepare pinaverium bromide, dihydronopol is first reacted with morpholinoethyl chloride by the method described in French Patent No. 2,097,031, and the resulting reaction product is further reacted with 2-bromo-4,5-dimethoxybenzyl bromide by the method described in U.S. Pat. No. 3,845,048 (=French Patent No. 2,097,032).

According to French Patent No. 2,097,031, dihydronopol is obtained by hydrogenation of the double bond from the terpene alcohol (−)-nopol (=2-((1R,5S)-6,6-dimethylbicyclo[3.1.1]hept-2-en-2-yl)ethanol) of formula III

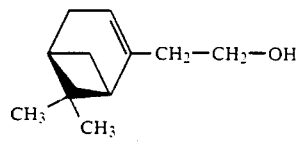
(III)

which is obtainable from (−)-β-pinene and, for example, disclosed in J. Am. Chem. Soc. 68 (1946), page 638. This hydrogenation is carried out at temperatures of 80°-100° C. in the presence of a platinum oxide catalyst (=Adams catalyst) or else in the presence of Raney nickel or Urushibara nickel. It is possible, if desired, to use a solvent, for example an alcohol.

The hydrogenation of (−)-nopol to dihydronopol by the method described in the French patent results in a mixture of stereoisomers which, besides a predominant content of cis compound, also contains a significant content of trans compound. The configuration at the ring structure is retained during further reaction of dihydronopol to produce pharmacologically active compounds, so that the pharmacologically active final products also are mixtures of stereoisomers. Where stereoisomerically pure compounds are required, these must be initially concentrated and finally isolated from stereoisomer mixtures by elaborate separation processes which are known per se and involve large losses.

It is generally the aim in preparing pharmaceuticals to use active compounds which are as pure as possible and sterically homogeneous. There is a continuing need for processes which can produce compounds having asymmetric centers which exhibit improved stereoisomeric purity.

SUMMARY OF THE INVENTION

It is therefore the object of the present invention to provide an improved process for the diastereoselective preparation of cis-dihydronopol and its esters.

It is also an object of the present invention to provide a process for preparing cis-dihydronopol or an ester thereof having greater stereoisomeric purity.

These and other objects of the invention are achieved by providing a process for preparing a 2-((1S,2S,5S)-6,6-dimethylbicyclo[3.1.1]hept-2-yl)-ethanol derivative corresponding to the formula I

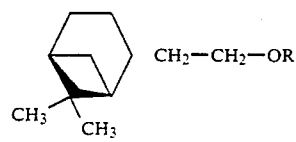
(I)

in which R represents hydrogen or an acyl group COR[1] in which R[1] denotes lower alkyl or phenyl which is optionally substituted by lower alkyl, lower alkoxy or hydroxyl, in which an ester corresponding to the formula II

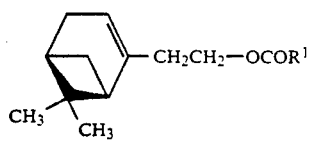
(II)

in which R[1] has the above meaning, is hydrogenated with hydrogen in the presence of a solid catalyst selected from the group consisting of platinum, platinum oxide and ruthenium/carbon to give a compound corresponding to the formula Ia

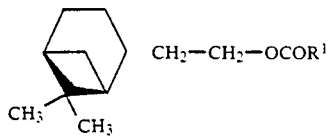

in which R[1] has the above meaning, and optionally eliminating the COR[1] group from the compound of formula Ia.

DETAILED DESCRIPTION OF PREFERRED EMBODIMENTS

A process with which cis-dihydronopol can be obtained in good yields and with high diastereoselectivity has now been found. The invention thus relates to a process for preparing 2-((1S,2S,5S)-6,6-dimethylbicyclo[3.1.1.hept-2-yl])-ethanol derivatives of the general formula I

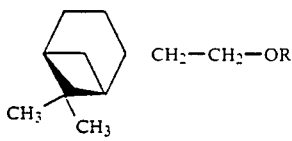

in which the substituent in the 2 position is cis with respect to the dimethylmethylene bridge, and R represents hydrogen or an acyl group COR[1] in which R[1] denotes lower alkyl or phenyl which is optionally substituted by lower alkyl, lower alkoxy or hydroxyl, characterized in that esters of the general formula II

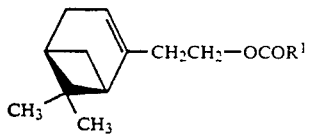

in which R[1] has the above meaning, are hydrogenated with hydrogen in the presence of a solid platinum or platinum oxide catalyst or ruthenium/carbon catalyst to give compounds of the general formula Ia

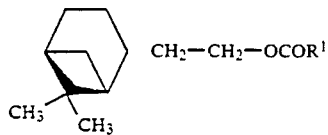

in which R[1] has the above meaning, and, if desired, the COR[1] group is eliminated from the compounds of formula Ia.

Where the substituent R of the compounds of the formula I contains lower alkyl groups, these can be straight-chain or branched and preferably contain 1 to 4, in particular 1 or 2, carbon atoms. Lower carboxylic esters corresponding to formula II, for example an acetate or propionate, preferably the acetate, are particularly suitable for use in the process of the invention.

The process according to the invention is a heterogeneous hydrogenation in the presence of a solid platinum or platinum oxide catalyst or ruthenium/carbon catalyst. It is possible to use as catalyst, for example, commercially available platinum oxide which has a platinum content of 79-85% and is known, for example, under the name "Adams catalyst". Platinum catalysts can be employed which are supported catalysts which contain platinum on an organic or inorganic support material, or platinum black. Suitable support materials for the supported catalysts are materials known per se for preparing catalyst supports. Thus, for example, active charcoal or else ceramic materials, for example aluminum oxides, silicon oxides and alumino-silicates, are suitable. The platinum content of such supported catalysts may be between 1 and 10% by weight, in particular 4 to 6% by weight, relative to the total weight of the catalyst. Examples which have proven advantageous include platinum/carbon catalysts with a platinum content of 3 to 7% by weight. Supported catalysts which contain ruthenium on a carbon support are also suitable. Examples which have proven advantageous include ruthenium/carbon catalysts with a ruthenium content of 1-10% by weight, preferably 3-7% by weight. The amount of catalyst to be used may vary depending on the nature of the catalyst employed and on the hydrogen pressure used and the reaction time. If a hydrogen pressure of about 80 bar is used, satisfactory yields generally can be obtained within 3-4 hours when platinum oxide is used in an amount of from about 1 to about 15 g of platinum oxide catalyst per mole of starting compound of formula II which is to be hydrogenated, and when platinum/carbon is used in an amount corresponding to from about 0.1 to about 1 g of platinum metal per mole of starting compound. If ruthenium/carbon catalysts are used and, for example, with a hydrogen pressure of 95 bar, satisfactory yields generally can be achieved within 4-5 hours with amounts of catalyst corresponding to from about 0.2 to about 1 g of ruthenium per mole of starting compound.

The hydrogenation can be carried out without the addition of another solvent or in the presence of an organic solvent. Suitable organic solvents include aliphatic, cycloaliphatic or aromatic hydrocarbons such as n-hexane, cyclohexane or toluene, open-chain or cyclic ethers such as tetrahydrofuran, lower alkyl esters of lower carboxylic acids such as, for example, ethyl acetate, lower ketones such as acetone or lower straight-chain or branched alkanols, for example lower alcohols with 1 to 4, and preferably 1 to 3, carbon atoms, in particular ethanol or isopropanol.

The hydrogenation can be carried out under a hydrogen pressure in the range from 1 to 100 bar. It is desirably carried out under elevated pressure, for example under a hydrogen pressure between 3 and 95 bar, preferably between 60 and 95 bar. When platinum or platinum oxide catalysts are used, it is generally possible to employ a lower hydrogen pressure than when ruthenium catalysts are used.

The hydrogenation can be carried out at room temperature or slightly elevated temperatures, for example at temperatures between 10° and 60° C., preferably 15° and 50° C., in particular from 18° to 25° C. The reaction time varies depending on the hydrogen pressure, temperature, type of catalyst and amount of catalyst used. It can be, for example, between 1 and 10 hours. In general, however, reaction of the starting compound is substantially complete after only 3 to 7 hours.

The cleavage of the esters of the formula Ia to yield the corresponding alcohol can be carried out by solvolysis in a known manner. Thus, the esters of the formula Ia can be cleaved under conditions customary for ester cleavage, for example by basic hydrolysis or alcoholysis. For example, the esters can be treated, in the presence of an inorganic or organic base, with water or a lower alcohol or a mixture thereof at temperatures between room temperature and the boiling point of the reaction mixture. Examples of suitable inorganic bases include alkali metal hydroxides or carbonates or alkaline earth metal hydroxides or carbonates, in particular potassium or sodium hydroxide. The cleavage can be carried out directly on the crude product obtained after the hydrogenation and removal of the catalyst and solvent without intervening purification or isolation.

Where necessary, the crude hydrogenation product compounds of the formula I which have been obtained after removal of the catalyst and solvent or after an ester cleavage subsequent thereto, can be purified in a known manner, for example by distillation or chromatography.

The process according to the invention has the advantage, compared with the hitherto known preparation of dihydronopol, that even at temperatures around room temperature there is rapid and complete reaction of the starting compounds, and the cis compounds of the formula I are obtained with good yields and high stereoselectivity. Thus, in general, total yields of compounds of the formula I of over 90%, for example between 95 and 100%, are obtained. The cis-dihydronopol prepared according to the invention generally contains less than 0.4%, frequently less than 0.2%, of trans-dihydronopol as an impurity.

The starting esters of the formula II can be obtained in a known manner by acylating the alcohol of formula III. For example, the alcohol of formula III can be reacted under the customary conditions for ester formation with a reactive acid derivative of formula IV $$R^1\text{-CO-X} \qquad (IV)$$

in which $R^1$ has the above meaning, and X denotes halogen or an $OCOR^1$ radical in which $R^1$ has the above meaning. The acetate of formula I can also be obtained in a known manner directly from $(-)$-$\beta$-pinene of formula B by reacting the latter with formaldehyde in glacial acetic acid.

The following examples are intended to illustrate the invention in further detail without restricting its scope.

EXAMPLE 1

Preparation of cis-dihydronopol.

A) 50 g of acetyl chloride (=0.64 mole) were slowly added dropwise to a solution of 100 g of (−)-nopol (=0.6 mole) and 130 ml of triethylamine (=0.93 mole) in 600 ml of dichloromethane while cooling in ice at a temperature of 5° to 10° C. The reaction mixture was subsequently stirred at 5° to 10° C. for a further 20 minutes. The reaction mixture was then further stirred without cooling until it had warmed to room temperature. To work up the reaction mixture, it was stirred into 800 ml of ice-water. The organic phase was separated, the aqueous phase was washed with 100 ml of dichloromethane, and the combined organic phases were washed to neutrality with saturated aqueous sodium bicarbonate solution and dried over sodium sulfate. The residue after removal of the dichloromethane by distillation was 130 g of crude product, from which (−)-nopyl acetate was isolated by fractional distillation. 98 g of (−)-nopyl acetate with a boiling point of 117°–119° C. (10 mm Hg) and a refractive index $n_D^{20} = 1.4722$ were obtained.

B) 20 g of (−)-nopyl acetate were dissolved in 150 ml of ethyl acetate at room temperature. The solution was mixed in a 1-liter autoclave with 1 g of powdered platinum oxide catalyst (=Adams catalyst, platinum content 82%). The autoclave containing the reaction mixture was flushed several times with nitrogen. The mixture was then hydrogenated at room temperature under a hydrogen pressure of 80 bar. Hydrogen uptake ceased after about 3 hours. The hydrogen was released, and the autoclave was flushed several times with nitrogen. The reaction solution was then filtered off from the catalyst and concentrated in a rotary evaporator. 20.3 g of crude cis-dihydronopyl acetate with a boiling point of 126°–128° C. (10 mm Hg) and a refractive index $n_D^{25} = 1.4685$ were obtained.

To determine the purity and the isomer ratio, the resulting crude cis-dihydronopyl acetate was analyzed by gas chromatography (=GC). A Sichromat type gas chromatograph manufactured by Siemens having a flame ionization detector and a fused silica capillary column which was 30 m long and 0.32 mm in internal diameter (WCOT 123-1334 type column from J. & W. Scientific) packed with immobilized silicone material as a stationary phase (Durabond DB 624 from J. & W. Scientific) was used for the gas chromatographic analysis. Helium was used as the carrier gas, with an inlet pressure of 0.6 bar and a flow rate of 30 cm/sec. An injection temperature of 200° C. and a temperature program for the column from 180° C. to 230° C. with a heating rate of 4° C./min and a detection temperature of 250° C. were used. For the analysis, 0.5 microliter of a 1% strength solution of the test substance in methanol was injected into the gas chromatograph which operated with a split of 1:25. The analysis yielded the following values:

| | |
|---|---|
| Total dihydronopyl acetate content: | 98.1% |
| Cis/trans ratio: | 99.8 to 0.2 |
| Unhydrogenated starting material content: | 0.3% |

C) 20 g of the crude cis-dihydronopyl acetate obtained in step B) were added dropwise to a solution of 6.5 g of potassium hydroxide in 30 ml of methanol, and the reaction mixture was stirred at room temperature under a nitrogen atmosphere for 2 hours. 150 ml of ether were then added to the reaction mixture, and the resulting mixture was washed 3 times with 75 ml of water each time. The combined aqueous washings were extracted with 75 ml of ether, and the combined ether phases were dried over sodium sulfate. Removal of the ether by distillation yielded 15.1 g of cis-dihydronopol as a colorless oil with a boiling point of 123° to 125° C. (10 mm Hg) and a refractive index $n_D^{25} = 1.4882$.

EXAMPLE 2

Preparation of cis-dihydronopyl acetate.

2.5 kg of (−)-nopyl acetate (prepared analogously to Example 1A) were dissolved in 15 liters of ethyl acetate, and the solution was placed in a 30 liter autoclave.

Subsequently a suspension of 90 g of powdered platinum oxide catalyst (=Adams catalyst) in 3 liters of ethyl acetate was added. The autoclave was flushed several times with nitrogen. Then hydrogen was introduced into the autoclave at a hydrogen pressure of 95 bar, and hydrogenation was carried out under this hydrogen pressure at a temperature of 13° to 23° C. for 135 minutes. The hydrogen was then released, and the autoclave was flushed several times with nitrogen. The reaction mixture was withdrawn from the autoclave and filtered to remove the catalyst. The autoclave was rinsed with 3 liters of ethyl acetate, and the catalyst was likewise washed with this rinsing liquid. The combined filtrates were concentrated. 2.456 kg of crude cis-dihydronopyl acetate (boiling point 126°–128° C. (10 mm Hg), refractive index $n_D^{25} = 1.4688$) were obtained. The product was investigated by gas chromatography as described in Example 1B and found to have the following composition:

| | |
|---|---|
| cis-dihydronopyl acetate | 98.7% |
| trans-dihydronopyl acetate | 0.2% |
| unreacted (−)-nopyl acetate | 0.1% |
| cis-dihydronopol | 0.2% |
| other volatile constituents | 0.8% |

This corresponds to a total yield of dihydronopyl acetate of 2.429 kg = 96.2% with a cis/trans ratio of 99.8 to 0.2.

The product was converted into cis-dihydronopol (boiling point 123°–125° C. (10 mm Hg)) as described in Example 1C.

EXAMPLE 3

Preparation of cis-dihydronopyl acetate.

150 g of (−)-nopyl acetate were mixed with 5 g of Adams catalyst in an autoclave without addition of any other solvent and hydrogenated as described in Example 1. Hydrogen uptake ceased after about 6 hours. After flushing with nitrogen, the hydrogenation product was worked up by being diluted with 0.5 liter of ethyl acetate and filtered to remove the catalyst. The catalyst was washed again with 50 ml of ethyl acetate. The filtrate and washing liquid were combined, and the solvent was removed by distillation. 151 g of crude cis-dihydronopyl acetate with a refractive index $n_D^{25} = 1.4689$ were obtained.

GC analysis:

| | |
|---|---|
| Total dihydronopyl acetate content: | 98.6% |
| Cis/trans ratio: quantitatively cis compound (i.e. no trans isomer detectable by GC analysis method described above). | |
| Unhydrogenated starting material content: | 0.2% |

EXAMPLE 4

Preparation of cis-dihydronopyl acetate.

20 g of (−)-nopyl acetate were dissolved in 150 ml of ethanol at room temperature. The solution was mixed in a 1 liter autoclave with 1 g of powdered ruthenium/carbon catalyst (ruthenium content 5%). The autoclave containing the reaction mixture was flushed several times with nitrogen. The mixture was then hydrogenated at room temperature under a hydrogen pressure of 95 bar for 7 hours. The hydrogen was then released, and the autoclave was flushed several times with nitrogen. The reaction solution was filtered to remove the catalyst and concentrated in a rotary evaporator. 20.3 g of crude cis-dihydronopyl acetate were obtained having a boiling point of 126°–128° C. (10 mm Hg) and a refractive index $n_D^{25} = 1.4682$.

GC analysis:

| | |
|---|---|
| Total dihydronopyl acetate content: | 98.9% |
| Cis/trans ratio: | 99.6 to 0.4 |
| Unhydrogenated starting material content: | 0.2% |

EXAMPLE 5

Preparation of cis-dihydronopyl acetate.

(−)-Nopyl acetate was hydrogenated at room temperature analogously to the methods described in Examples 1 to 4 under the reaction conditions indicated in the following Table I. The hydrogenation was stopped after 3 hours at the latest, filtered to remove the catalyst, concentrated, and the resulting hydrogenation product was analyzed by gas chromatography as described in Example 1B. Besides the reaction conditions, Table I also indicates the degree of conversion of the starting material attained after a reaction time of 3 hours, and the cis/trans ratio in the final product.

TABLE I

| Example No. | Catalyst grams per 20 g of precursor | Solvent | H$_2$ Pressure in bar | Conversion = % reacted starting material | cis/trans ratio in the final product |
|---|---|---|---|---|---|
| 5a** | 1 g PtO$_2$ | Ethyl acetate | 95–100 | 99.9 | 99.83:0.17 |
| 5b | 1 g PtO$_2$ | Ethyl acetate | 70 | 99.7 | 99.80:0.20 |
| 5c | 1 g PtO$_2$ | Ethyl acetate | 50 | 99.9 | 99.82:0.18 |
| 5d | 1 g PtO$_2$ | Ethyl acetate | 30 | 85.1 | 99.78:0.22 |
| 5e | 1 g PtO$_2$ | n-Hexane | 80 | 86.2 | 99.88:0.12 |
| 5f | 1 g PtO$_2$ | Toluene | 80 | 90.1 | 99.77:0.23 |
| 5g | 1 g PtO$_2$ | Tetrahydrofuran | 80 | 97.1 | quantitatively cis* |
| 5h | .67 g PtO$_2$ | — | 80 | 89.7 | quantitatively cis* |
| 5i | 1 g PtO$_2$ | Acetone | 80 | 92.2 | quantitatively cis* |
| 5j | 1 g PtO$_2$ | C$_2$H$_5$OH | 80 | 98.7 | quantitatively cis* |
| 5k | 1 g PtO$_2$ | CH$_3$OH | 80 | 97.4 | quantitatively cis* |
| 5l | 1 g PtO$_2$ | (CH$_3$)$_2$CHOH | 80 | 99.8 | quantitatively cis* |
| 5m | 1 g Pt/C(5%) | C$_2$H$_5$OH | 80 | 86.4 | 99.66:0.34 |
| 5n*** | 1 g PtO$_2$ | Ethyl acetate | 95 | 99.7 | 99.85:0.15 |

TABLE I-continued

| Example No. | Catalyst grams per 20 g of precursor | Solvent | H₂ Pressure in bar | Conversion = % reacted starting material | cis/trans ratio in the final product |
|---|---|---|---|---|---|
| 5o**** | 1 g Ru/C(5%) | C₂H₅OH | 95 | 95.3 | 99.59:0.41 |

*quantitatively cis = no trans product detectable, i.e. trans << 0.1%
**reaction time only 2.5 hours
***reaction time only 1 hour
****reaction time 4 hours, reaction temperature 50° C.

EXAMPLE 6

Preparation of cis-dihydronopyl propionate.

A) 75 g of (−)-nopol were dissolved together with 97 ml of triethylamine in 500 ml of dichloromethane as in Example 1A, and the solution was reacted with 40.9 g of propionyl chloride. The reaction mixture was worked up as described in Example 1A. Two fractional distillations resulted in 54.6 g of nopyl propionate having a boiling point of 136°-138° C. (10 mm Hg).

B) 20 g of nopyl propionate were hydrogenated by the method described in Example 1B at room temperature and under a hydrogen pressure of 80 bar in the presence of Adams catalyst in ethanol. The hydrogenation was stopped after 3 hours, and the reaction mixture was worked up as described in Example 1B. 20.5 g of crude cis-dihydronopyl propionate having a refractive index $n_nD^{20} = 1.4668$ were obtained.

The resulting crude cis-dihydronopyl propionate was analyzed by gas chromatography as described in Example 1B except the column which was used was a fused silica column (Chrompack, WCOT 7745) which was 25 m long and had an internal diameter of 0.32 mm and was packed with a polysilicone material stationary phase (Chrompack, CP-Sil 43CB; 0.2 micron, organic radicals 50% methyl, 25% cyanopropyl, 25% phenyl groups). The injector temperature was 200° C., the temperature program for the column was 160°-220° C. with a heating rate of 3° C./minute. Gas chromatography analysis yielded the following values:

| Total dihydronopyl propionate content: | 94.1% |
|---|---|
| Cis/trans ratio: | 99.9 to 0.1 |
| Unhydrogenated starting material content: | 1.3% |

The resulting crude cis-dihydronopyl propionate can be converted into cis-dihydronopol as described in Example 1C.

EXAMPLE 7

Preparation of cis-dihydronopyl benzoate.

A) 49.9 g of (−)-nopol were dissolved together with 65 ml of triethylamine in 350 ml of dichloromethane analogously to Example 1A, and the reaction mixture was reacted with 43.3 g of benzoyl chloride. The reaction mixture was then worked up analogously to Example 1A. Fractional distillation resulted in 51.1 g of nopyl benzoate having a boiling point of 179°-182° C. (1 mm Hg).

B) 26 g of nopyl benzoate were dissolved in 150 ml of ethanol analogously to Example 1B and hydrogenated in the presence of 1 g of Adams catalyst at room temperature and under a hydrogen pressure of 80 bar. The hydrogenation was stopped after 8 hours and the reaction mixture was worked up analogously to Example 1B. 25.4 g of crude cis-dihydronopyl benzoate with a refractive index $n_D^{20} = 1.5295$ were obtained. This was investigated by gas chromatography as described in Example 6B. Gas chromatography analysis:

| Total dihydronopyl benzoate content: | 92.4% |
|---|---|
| Cis/trans ratio: | 99.8 to 0.2 |
| Unhydrogenated starting material content: | 3.3% |

The resulting crude cis-dihydronopyl benzoate can be converted into cis-dihydronopol as described in Example 1C.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all modifications falling within the ambit of the appended claims and equivalents thereof.

What is claimed is:

1. A process for preparing a 2-((1S,2S,5S)-6,6-dimethylbicyclo[3.1.1]hept-2-yl)-ethanol derivative corresponding to the formula I

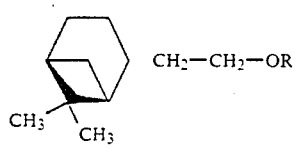

(I)

in which R represents hydrogen or an acyl group COR¹ in which R¹ denotes lower alkyl or phenyl which is optionally substituted by lower alkyl, lower alkoxy or hydroxyl, wherein an ester corresponding to the formula II

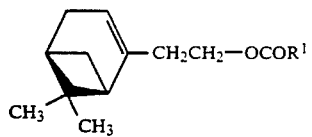

(II)

in which R¹ has the above meaning, is hydrogenated with hydrogen in the presence of a solid catalyst selected from the group consisting of platinum, platinum oxide and ruthenium/carbon to give a compound corresponding to the formula Ia

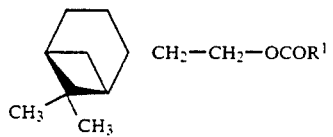

(Ia)

in which R¹ has the above meaning, and optionally eliminating the COR¹ group from the compound of formula Ia.

2. A process according to claim 1, wherein said COR¹ group is an acetyl group.

3. A process according to claim 1, wherein the hydrogenation is carried out at temperatures in the range from 15° to 50° C.

4. A process according to claim 3, wherein the hydrogenation is carried out at temperatures in the range from 18° to 25° C.

* * * * *